(12) United States Patent
Maity et al.

(10) Patent No.: US 9,103,704 B2
(45) Date of Patent: Aug. 11, 2015

(54) HOLDING DEVICE TO HOLD A REFLECTOR AND AN ELECTROMAGNETIC GUIDING DEVICE

(71) Applicant: General Electric Company, Schenectady, NY (US)

(72) Inventors: Sandip Maity, Bangalore (IN); Saroj Kumar Mahalik, Bangalore (IN); Vinayak Tilak, Bangalore (IN); Mason Harvey Guy, Hook (GB); Neil Geoffrey Harris, Woodley (GB); Stuart John Eaton, Sunbury on Thames (GB)

(73) Assignee: General Electric Company, Niskayuna, NY (US)

( * ) Notice: Subject to any disclaimer, the term of this patent is extended or adjusted under 35 U.S.C. 154(b) by 82 days.

(21) Appl. No.: 13/950,351

(22) Filed: Jul. 25, 2013

(65) Prior Publication Data
US 2015/0027243 A1 Jan. 29, 2015

(51) Int. Cl.
| | |
|---|---|
| *G01N 15/00* | (2006.01) |
| *G01D 11/30* | (2006.01) |
| *E21B 47/12* | (2012.01) |
| *G01N 21/552* | (2014.01) |
| *G01N 21/85* | (2006.01) |

(52) U.S. Cl.
CPC .............. *G01D 11/30* (2013.01); *E21B 47/122* (2013.01); *E21B 47/123* (2013.01); *G01N 21/552* (2013.01); *G01N 21/8507* (2013.01); *G01N 2021/8528* (2013.01); *G01N 2201/084* (2013.01)

(58) Field of Classification Search
CPC .......... G01D 11/30; G01N 2021/8528; G01N 21/552

USPC .......................................... 73/800, 856, 866.5
See application file for complete search history.

(56) References Cited

U.S. PATENT DOCUMENTS

| | | | |
|---|---|---|---|
| 4,712,915 A | * | 12/1987 | Kosakowski et al. .... 356/139.08 |
| 5,166,747 A | | 11/1992 | Schroeder et al. |
| 5,831,743 A | | 11/1998 | Ramos et al. |
| 5,956,132 A | | 9/1999 | Donzier |
| 6,016,702 A | | 1/2000 | Maron |

(Continued)

FOREIGN PATENT DOCUMENTS

| | | |
|---|---|---|
| GB | 2449933 A | 12/2008 |
| JP | 10038801 A | 2/1998 |

OTHER PUBLICATIONS

Fordham et al., "Multi-Phase-Fluid Discrimination with Local Fibre-Optical Probes: II. Gas/liquid Flows", Measurement Science and Technology, vol. 10, Issue 12, 1999, pp. 1338-1346.

(Continued)

*Primary Examiner* — Max Noori
(74) *Attorney, Agent, or Firm* — Scott J. Asmus

(57) ABSTRACT

A holding is presented. The holding device includes a male connector comprising a first male extension and a second male extension that extend out of opposite surfaces of a male central disk, an electromagnetic guiding device continuously passing through a central hole that continuously passes through the first male extension, the male central disk and the second male extension, a reflector that is in a direct physical contact with a first end of the electromagnetic guiding device that ends at a top surface of the first male extension, and a holder that covers the first male extension to hold the reflector, and maintain the physical contact between the first end of the electromagnetic guiding device and the reflector.

20 Claims, 14 Drawing Sheets

(56) References Cited

U.S. PATENT DOCUMENTS

| | | | |
|---|---|---|---|
| 6,298,572 B1* | 10/2001 | McAuley | 33/573 |
| 7,044,219 B2 | 5/2006 | Mason et al. | |
| 7,255,173 B2 | 8/2007 | Hosie et al. | |
| 7,880,133 B2 | 2/2011 | Johansen | |
| 8,039,793 B2 | 10/2011 | Lievois et al. | |
| 8,174,699 B2 | 5/2012 | Baleine | |
| 8,218,133 B2 | 7/2012 | Wootten | |
| 2005/0128462 A1* | 6/2005 | Matsui | 355/72 |
| 2007/0108378 A1 | 5/2007 | Terabayashi et al. | |
| 2010/0145634 A1 | 6/2010 | Pinguet et al. | |
| 2010/0299068 A1 | 11/2010 | Mason et al. | |
| 2011/0068990 A1* | 3/2011 | Grzyb et al. | 343/772 |
| 2012/0046870 A1 | 2/2012 | Lievois et al. | |
| 2012/0081698 A1 | 4/2012 | Christian et al. | |
| 2013/0009048 A1 | 1/2013 | Xie et al. | |

OTHER PUBLICATIONS

S. Sainov, "Optical Sensor Based on Total Internal Reflection Diffraction Grating", Sensors and Actuators A: Physical, vol. 45, Issue 1, Oct. 1994, pp. 1-6.

M J Da Silva et al., "Phase Fraction Distribution Measurement of Oil—Water Flow Using a Capacitance Wire-Mesh Sensor", Measurement Science and Technology, vol. 22, Issue 10, 2011, 104020 (9pp).

* cited by examiner

HOLDING DEVICE TO HOLD A REFLECTOR AND AN ELECTROMAGNETIC GUIDING DEVICE

BACKGROUND

While there are many efforts related to alternative energy sources, fossil fuel remains a major economic driver. Accordingly, the interest in developing new fossil fuel production fields continues to remain strong. In developing a new fossil fuel production field, a well is drilled. A well may have a mix of different fluids including oil, water, gas, and other hydrocarbons. It is typically desirable to assess the mix of different fluids in the well before developing a new production field. Furthermore, it may be desirable to assess the mix of different fluids for assessing the remaining life of a fossil fuel production field.

While assessing the mix of different fluids in a well, harsh environmental conditions may be encountered. For example, pressure in the well may exceed fifteen-thousand to twenty-thousand (15,000-20,000) pounds per square inch and the temperature may exceed one-hundred-eighty (180) degrees Celsius. Accordingly, current technologies for assessing the mix of different fluids in the well are typically suitable for such harsh environmental conditions. Examples of current technologies for assessing the mix of different fluids in a well may include capacitance and resistance array sensors. However, the range of technologies for assessing the mix of fluids in the well is limited. Also, it is desirable to improve the sensitivity of the current technologies for assessing the mix of different fluids. Therefore, it may be desired to provide a novel approach for analyzing the mix of fluids in a well.

BRIEF DESCRIPTION

A device is presented. The device includes an electromagnetic guiding device to provide electromagnetic radiation, a reflector that reflects a portion of the electromagnetic radiation to generate a reflected portion of the electromagnetic radiation, wherein the reflector is fully immersed in a multiphase fluid, and a processing subsystem that analyzes the multiphase fluid based upon at least a portion of the reflected portion of the electromagnetic radiation, wherein a principal optical axis of the electromagnetic guiding device substantially aligns with a principal optical axis of the reflector.

A device is presented. The device includes a primary coupling device coupled to an optical fiber, wherein the primary coupling device splits electromagnetic radiation into a first electromagnetic radiation part and a second electromagnetic radiation part, and directs the first electromagnetic radiation part through the optical fiber to irradiate a reflector immersed in a multiphase fluid, wherein the reflector reflects a portion of the first electromagnetic radiation part to generate reflected portion of the first electromagnetic radiation part, and a processing subsystem that determines the concentration of a fluid of interest, a gas to liquid phase fraction, or a combination thereof in the multiphase fluid based upon the intensity of at least a portion of the reflected portion of the first electromagnetic radiation part and the intensity of the second electromagnetic radiation part, wherein a principal optical axis of the reflector is aligned with a principal optical axis of the optical fiber, and an end of the optical fiber is in physical contact with the reflector.

A system is presented. The system includes a subsystem immersed in a multiphase fluid in a reservoir, wherein the subsystem comprises one or more devices mounted on respective bow string, wherein at least one of the one or more devices comprise a primary coupling device coupled to a first electromagnetic guiding device and a second electromagnetic guiding device, wherein the primary coupling device splits electromagnetic radiation into a first electromagnetic radiation part and a second electromagnetic radiation part, directs the first electromagnetic radiation part through the first electromagnetic guiding device to irradiate a reflector immersed in a multiphase fluid, wherein the reflector reflects a portion of the first electromagnetic radiation part to generate reflected portion of the first electromagnetic radiation part, a processing subsystem that analyze the multiphase fluid based upon the intensity of at least a portion of the reflected portion of the first electromagnetic radiation part and the intensity of the second electromagnetic radiation part, wherein a principal optical axis of the reflector is substantially aligned with a principal optical axis of the first electromagnetic guiding device, and a computing and display device located outside the reservoir, and communicatively coupled to the subsystem to receive signals representative of analysis results of the multiphase fluid.

A method is presented. The method includes steps of splitting electromagnetic radiation into a first electromagnetic radiation part and a second electromagnetic radiation part, directing the first electromagnetic radiation part to irradiate a reflector immersed in a multiphase fluid, generating a reflected portion of the first electromagnetic radiation part by reflecting a portion of the first electromagnetic radiation part by the reflector, splitting the reflected portion of the first electromagnetic radiation part into a first split reflected portion and a second split reflected portion, and analyzing the multiphase fluid based upon the first split reflected portion and the second electromagnetic radiation part.

DRAWINGS

These and other features and aspects of embodiments of the present invention will become better understood when the following detailed description is read with reference to the accompanying drawings in which like characters represent like parts throughout the drawings, wherein.

DETAILED DESCRIPTION

Existing tools/devices/instruments including array tools and non-array tools are typically used for production logging techniques and investigative logging techniques. The multiphase fluid, for example, may include gas, water, and liquid hydrocarbons including oil. The tools, for example, may include a water hold up tool, a density tool, a gas hold up tool, and the like. The existing tools are typically used to identify the presence of a fluid in a multiphase fluid. However, the existing tools are incapable or lack sensitivity to determine concentration and differentiate gas from liquid in the multiphase fluid. In addition, with the increased momentum towards directional wells and horizontal wells having complex flow of the multiphase fluid, phase fraction determination, concentration determination, and precise differentiation of fluids in the multiphase fluid becomes more complex. Therefore, advanced systems and techniques that may operate in these complex environments, and also determine the presence, concentration, and phase fraction of a fluid in the multiphase fluid is desired.

A technical effect of the present systems and methods is to provide production logging techniques and investigative logging techniques. In one embodiment, the present systems and methods analyze a multiphase fluid to determine the presence of a fluid in the multiphase fluid, concentration of the fluid in the multiphase fluid, and natural gas to liquid phase fraction. In another embodiment, the present systems and methods analyze the multiphase fluid to determine the presence and concentration of each fluid in the multiphase fluid. The multiphase fluid, for example, may include natural gas, water, oil, other hydrocarbons, or the like. In one embodiment, the present systems and methods differentiate natural gas from liquid with improved precision. The present systems and methods may analyze the multiphase fluid in different types of flows including flows in directional wells and horizontal wells. Furthermore, the present systems and methods analyze the multiphase fluid in a conduit or well without collecting a sample of the multiphase fluid outside or inside the conduit or well. Additionally, the present systems and methods analyze the multiphase fluid inside the well or conduit in real-time, for example in milliseconds.

Figure 1:
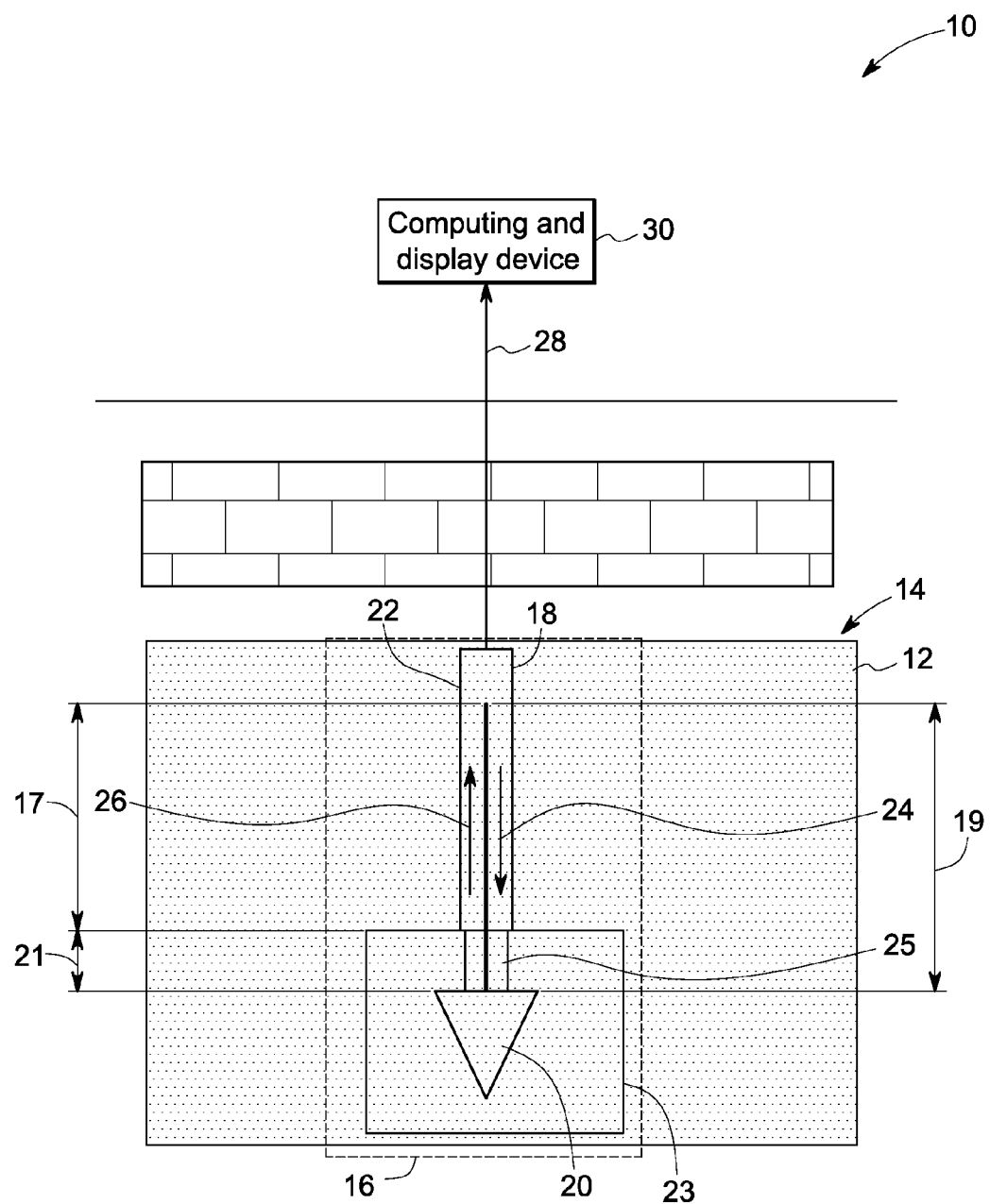
FIG. 1 is a block diagram of a system to perform production logging techniques and investigative logging techniques in a conduit, in accordance with one embodiment of the present systems.

Referring to FIG. 1, a block diagram of a system 10 to perform production logging techniques and investigative logging techniques is presented. The system 10 analyzes a multiphase fluid 12 in a conduit 14 to perform the production logging techniques and the investigative logging techniques. The conduit 14, for example, may be in an oil well, a fossil fuel well, or a potential area for becoming an oil well/fossil fuel well. The system 10 includes a device 16 to analyze the multi-phase fluid 12. As shown in FIG. 1, the device 16 is fully immersed in the multi-phase fluid 12. In the presently contemplated configuration, the device 16 analyzes the multi-phase fluid 12 in-situ, and is immersed in the multiphase fluid 12. In one example, the device 16 does not collect a sample of the multi-phase fluid 12 to analyze the multi-phase fluid 12 in a lab or otherwise external to the conduit 14. In another example the device 16 analyzes the multi-phase fluid 12 in real-time.

As will be described in greater detail, the device 16 is relatively impervious and resistant to the harsh conditions of the conduit 14. In a non-limiting example, the device 16 may withstand pressure in a range of about fifteen-thousand to twenty-thousand (15,000-20,000) pounds per square inch and a temperature range of about 180 degrees Celsius to 200 degrees Celsius.

As shown in the presently contemplated configuration, the device 16 includes a first portion 18 and a second portion 23. As described in greater detail with reference to FIG. 2, the first portion 18 includes a plurality of components (not shown in FIG. 1) to generate electromagnetic radiation and transmit that radiation to the second portion 23. The components in the first portion 18 are covered by a casing 22 which in one example is made of titanium. In certain embodiments, the casing 22 may be made of stainless steel, Inconel, brass, or the like.

The device 16 includes an electromagnetic guiding device 19. In FIG. 1, the first portion 18 includes a first portion 17 of the electromagnetic guiding device 19 and the second portion 23 includes a second portion 21 of the electromagnetic guiding device 19, wherein the electromagnetic guiding device 19 extends from the wave source (not shown) to a reflector 20. The electromagnetic guiding device 19, for example comprises a hollow core fiber, a photonic band gap fiber, a liquid fiber, or the like. In the presently contemplated configuration, the electromagnetic guiding device 19 is an optical fiber. The electromagnetic guiding device 19, for example, may be a single piece or be composed of multiple pieces or sections that are joined or coupled together. The electromagnetic guiding device 19, in one example may have a diameter in the range of about 280 microns to about 310 microns. In a non-limiting example, the length of the electromagnetic guiding device 19 is about 2 meters. The length of the electromagnetic guiding device 19 may depend upon the configuration of the system 10. In certain embodiments, the electromagnetic guiding device 19 may have a coating of carbon, hydrogen capturing gels, or the like to prevent formation of hydroxyl due to the presence of free hydrogen atoms inside the conduit 14.

In the presently contemplated configuration, the second portion 23 includes the reflector 20 and the second portion 21 of the electromagnetic guiding device 19. The reflector 20, for example may be a retroreflector, a corner cube reflector, a chamfered corner cube reflector, a corner cube prism, a chamfered corner cube prism, corner cube retroreflector, a chamfered corner cube retroreflector, a lens, a cone, or the like. An exemplary corner cube retroreflector is shown with reference to FIG. 5. Additionally, an exemplary chamfered corner cube retroreflector is shown with reference to FIG. 6.

As shown in the presently contemplated configuration, the reflector 20 is completely immersed in the multiphase fluid 12, and the reflector 20 is in a direct physical contact with the multiphase fluid 12. As previously noted, the conduit 14 has very harsh conditions. For example, based upon the depth of the conduit 14, the pressure of the multi-phase fluid 12 may be in the range of about 15,000-20,000 pounds per square, and the temperature of the multi-phase fluid 12 may exceed one-hundred-eighty (180) degrees Celsius. Accordingly, the reflector 20 is made of a material that can withstand and is impervious to the harsh conditions inside the conduit 14. The reflector 20, for example, may be made of sapphire, ruby, diamond, glass, a high refractive index optical glass, LASF 35, or other materials that may withstand harsh conditions in the conduit 14.

As used herein, the term "fluid of interest" refers to a fluid which is of interest, and therefore the presence, concentration of the fluid in a multiphase fluid or a phase fraction of the fluid with respect to another fluid in the multiphase fluid is to be determined. The fluid of interest, for example, may include gas, natural gas, water, oil, crude oil, and other hydrocarbons, or the like. It is noted that the refractive index of reflector 20 is higher, lower, or equal to the refractive of the fluid of interest in the multi-phase fluid 12. In one embodiment, the refractive index of the reflector 20 is higher, lower, or equal to the refractive index of each fluid in the multi-phase fluid 12.

The device 16 includes the wave source (not shown) that irradiates electromagnetic radiation 24 into the reflector 20. The wave source (not shown) irradiates the electromagnetic radiation 24 into the reflector 20 via the electromagnetic guiding device 19. It is noted, that for ease of understanding, the electromagnetic radiation 24 is shown via a separate arrow, however, the electromagnetic radiation 24 passes through the electromagnetic guiding device 19.

As shown in FIG. 1, the second portion 21 of the electromagnetic guiding device 19 is in physical contact with the reflector 20. It is noted that the second portion 21 of the electromagnetic guiding device 19 may be covered by a tube 25. It is noted that the first portion 17 and the second portion 21 of the electromagnetic guiding device 19 is not in a direct physical contact with the multiphase fluid 12. The tube 25, for example, may be made of a composite, a metal, plastic, and the like. Furthermore, a principal optical axis of the reflector 20 is substantially aligned with a principal optical axis of the electromagnetic guiding device 19. The principal optical axis of a reflector and the principal optical axis of an electromagnetic guiding device are substantially aligned when:

1. The principal optical axis of the reflector and the principal optical axis of the electromagnetic guiding device are parallel and substantially fall on a single straight line; or
2. The principal optical axis of the reflector and the principal optical axis of the electromagnetic guiding device are parallel, and a distance between the principal optical axis of the reflector and the principal optical axis of the electromagnetic guiding device is in the range of about 0 to 30 micron.

The electromagnetic radiation 24, for example, may be infrared rays, visible light, laser, and the like. The electromagnetic radiation 24 in one example is irradiated along the principal optical axis of the reflector 20. Due to an optimal shape, an optimal angle, and an optimal size of the reflector 20, the electromagnetic radiation 24 is incident at an optimal angle of incidence into the reflector 20. It is noted that the wave source (not shown) may be controlled to emit the electromagnetic radiation 24 at a determined output power.

When the electromagnetic radiation 24 is irradiated into the reflector 20, part of the electromagnetic radiation 24 is reflected, refracted, or absorbed by the reflector 20 based upon the refractive index of the fluid of interest. In the presently contemplated configuration, a portion 26 of the electromagnetic radiation 24 is reflected by the reflector 20. In one embodiment, the portion 26 may comprise of about 3% to about 80% of the electromagnetic radiation 24. Hereinafter, the term "portion 26" will be referred to as "reflected portion 26 of the electromagnetic radiation 24."

In one embodiment, the first portion 18 analyzes the multiphase fluid 12 based upon the reflected portion 26 of the electromagnetic radiation 24. In one embodiment, the first portion 18 generates analysis results of the multiphase fluid 12 based upon the reflected portion 26 of the electromagnetic radiation 24. The analysis results, for example, may include information about the presence or absence of the fluid of interest in the multiphase fluid 12, concentration of the fluid of interest in the multiphase fluid 12, phase fraction, natural gas to liquid phase fraction, remaining life of the conduit 14, or combinations thereof. In certain embodiments, the device 16 determines the concentration of the fluid of interest or the natural gas to liquid phase fraction in the multiphase fluid 12 based upon the reflected portion 26 of the electromagnetic radiation 24. In the presently contemplated configuration, the device 16 generates signals 28 that are representative of the analysis results of the multiphase fluid 12.

The system 10 further includes a computing and display device 30 that is located external to the conduit 14. The computing and display device 30 is in operational communication with the device 16. In this embodiment, the computing and display device 30 is in a physical communication with the device 16 via a wire or wireless means. The computing and display device 30 receives the signals 28 from the device 16. A user (not shown) may view the analysis results via the computing device 30. For example, a user may view the presence/absence or concentration of the fluid of interest in the multiphase fluid 12 or natural gas to liquid phase fraction via the computing device 30. Furthermore, the user may further analyze the signals 28 via the computing device 30. In certain embodiments, the device 16 may be used as transducer in an instrument having a plurality of sensing devices to analyze the multiphase fluid 12. An exemplary instrument including a plurality of sensing devices, such as, the device 16 is shown with reference to FIG. 3.

Figure 2:
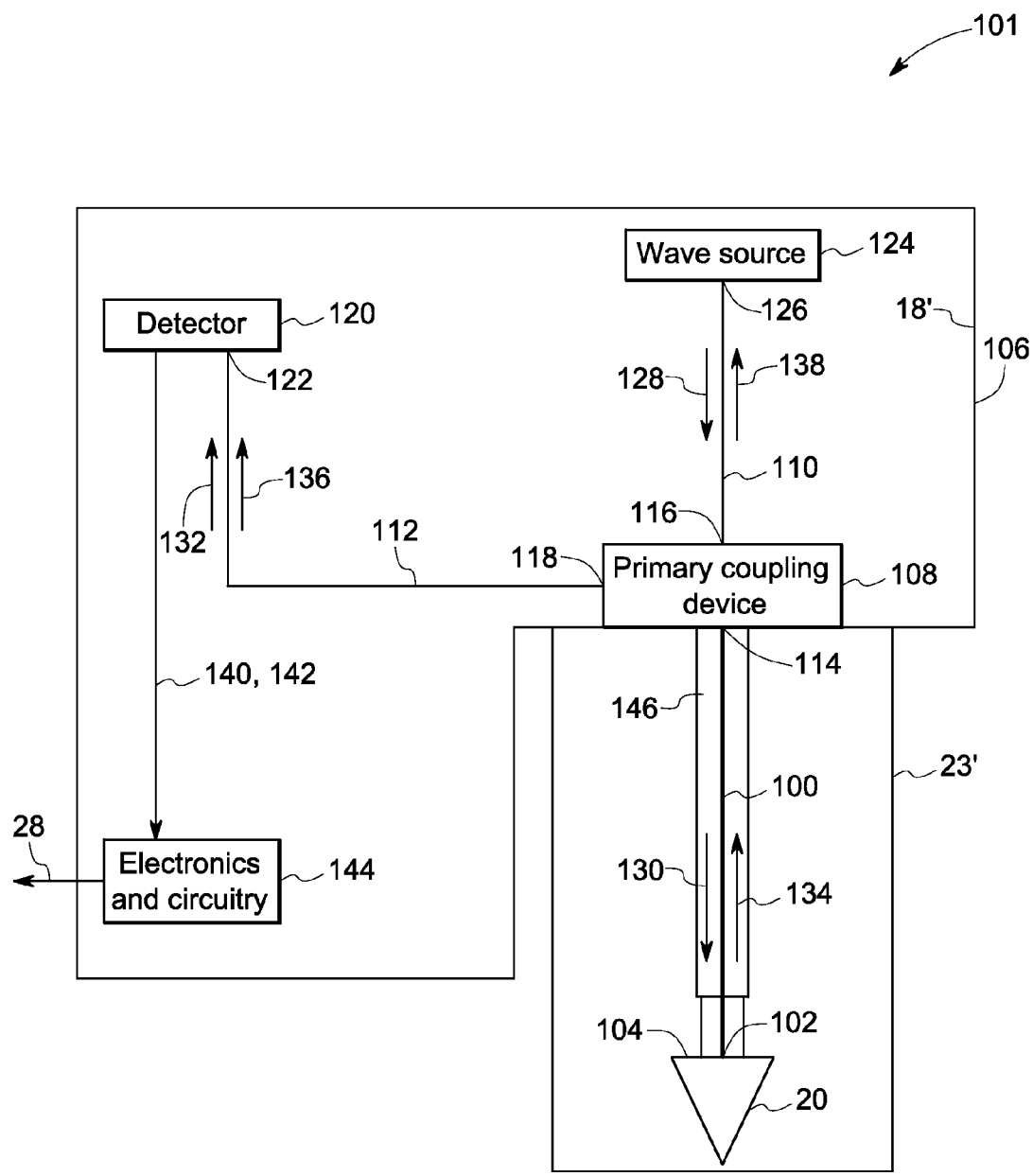
FIG. 2 is a block diagram of a device to perform production logging techniques and investigative logging techniques in a conduit, in accordance with certain aspects of the present systems.

FIG. 2 is a block diagram of a device 101 to perform production logging techniques and investigative logging techniques, in accordance with certain aspects of the present systems. In one embodiment, the device 101 is the device 16 (see FIG. 1). Similar to the device 16 referred to in FIG. 1, the device 101 has a first portion 18' and a second portion 23'. In one embodiment, the first portion 18' is the first portion 18, and the second portion 23' is the second portion 23 referred to in FIG. 1. The second portion 23' includes the reflector 20 (see FIG. 1) and a first electromagnetic guiding device 100. The first electromagnetic guiding device 100, for example, may be the second portion 21 of the electromagnetic guiding device 19 referred to in FIG. 1. A first end 102 of the first electromagnetic guiding device 100 is in a physical contact with the reflector 20. As shown in FIG. 2, the first end 102 of the first electromagnetic guiding device 100 is in physical contact with a base 104 of the reflector 20.

Furthermore, the first portion 18' of the device 101 includes a primary coupling device 108. The primary coupling device 108, for example is a coupler, a circulator, or the like. The primary coupling device 108 couples the first electromagnetic guiding device 100, a second electromagnetic guiding device 110 and a third electromagnetic guiding device 112. The primary coupling device 108 is coupled to a second end 114 of the first electromagnetic guiding device 100, a first end 116 of the second electromagnetic guiding device 110, and a first end 118 of the third electromagnetic guiding device 112.

The primary coupling device 108, for example, may be coupled to the first end 116 of the second electromagnetic guiding device 110 and to the second end 114 of the first electromagnetic guiding device 100 via one or more connectors (not shown). Similarly, the principal coupling device 108, for example, may be coupled to the first end 118 of the third electromagnetic guiding device 112 via one or more connectors (not shown). The connectors (not shown), for example, may be an optical connector or a mechanical connector. Accordingly, the primary coupling device 108 couples the second end 114 of the first electromagnetic guiding device 100 to the first end 116 of the second electromagnetic guiding device 110 and the first end 118 of the third electromagnetic guiding device 112.

Furthermore, the device 101 includes a detector 120 that is coupled to a second end 122 of the third electromagnetic guiding device 112. Accordingly, the detector 120 is coupled to the primary coupling device 108 via the third electromagnetic guiding device 112. In other words, the third electromagnetic guiding device 112 couples the detector 120 to the primary coupling device 108. The detector 120, for example, is an optical detector that converts optical signals to electrical signals. In one embodiment, the first electromagnetic guiding device 100 and the second electromagnetic guiding device 110 may together be referred to as the electromagnetic guiding device 19 (see FIG. 1).

The device 101 includes a wave source 124 that is coupled to a second end 126 of the second electromagnetic guiding device 110. For example, the wave source 124 may be a coherent source, an incoherent source, a visible light source, an infrared source, or the like. The coherent source may be a laser source. The incoherent source may be a Light Emitting Diode (LED). The wave source 124, for example, may be coupled to the second end 126 of the second electromagnetic guiding device 110 via a connector (not shown). The connector (not shown), for example, may be an optical connector or a mechanical connector. In the presently contemplated configuration, the wave source 124 is a laser source. Therefore, hereinafter, the term "wave source 124" is referred to as laser source 124. Since the laser source 124 is used in harsh conditions inside the conduit 14 (shown in FIG. 1), the laser source 124, for example, may sustain temperature exceeding 200° C., and pressure above 20000 psi.

In the presently contemplated configuration, the laser source 124 generates electromagnetic radiation 128. The laser source 124 directs the electromagnetic radiation 128 through the second electromagnetic guiding device 110 to the primary coupling device 108. In the presently contemplated configuration, the primary coupling device 108 is a 50:50 coupler that splits an input into two equal parts. In this example, the primary coupling device 108 splits the electromagnetic radiation 128 into a first electromagnetic radiation part 130 and a second electromagnetic radiation part 132. Because in the presently contemplated configuration, the primary coupling device 108 is a 50:50 coupler, each of the first electromagnetic radiation part 130 and the second electromagnetic radiation part 132 has substantially half intensity of the electromagnetic radiation 128. Accordingly, the first electromagnetic radiation part 130 and the second electromagnetic radiation part 132 have substantially equal intensity. The first electromagnetic radiation part 130, for example, may be the electromagnetic radiation 24 (see FIG. 1).

Subsequent to the primary coupling device 108 splitting of the electromagnetic radiation 128 into the first electromagnetic radiation part 130 and the second electromagnetic radiation part 132, the primary coupling device 108 directs the first electromagnetic radiation part 130 through the first electromagnetic guiding device 100 into the reflector 20, and the second electromagnetic radiation part 132 through the third electromagnetic guiding device 112 to the detector 120. Accordingly, the first electromagnetic guiding device 100 irradiates the reflector 20 by the first electromagnetic radiation part 130.

It is noted that for ease of understanding, the electromagnetic radiation 128, the first electromagnetic radiation part 130 and the second electromagnetic radiation part 132 are shown via separate arrows. In this example, the electromagnetic radiation 128 is transmitted through the second optical fiber 110, the first electromagnetic radiation part 130 is transmitted through the first optical fiber 100, and the second electromagnetic radiation part 132 is transmitted through the third optical fiber 112.

As previously noted, the reflector 20 is completely immersed in the multiphase fluid 12, and is in direct physical contact with the multiphase fluid 12. The irradiation of the reflector 20 results in reflection of a portion 134 of the first electromagnetic radiation part 130 by the reflector 20. The amount of reflection of the portion 134 of the first electromagnetic radiation part 130 depends upon the refractive index (referred to FIG. 1) of the fluid of interest and the presence/absence of the fluid of interest (referred to in FIG. 1) in the multiphase fluid 12. Hereinafter the phrase "portion 134 of the first electromagnetic radiation part 130" shall be interchangeably used with the term "reflected portion 134" or the term "reflected portion 134 of the first electromagnetic radiation part 130." It is noted that the reflected portion 134 of the first electromagnetic radiation part 130 may be about 0% to about 80% of the first electromagnetic radiation part 130 or the second electromagnetic radiation part. For example, when the fluid of interest is oil, and oil is present in the multiphase fluid 12, the reflected portion 134 is around 0% to 3% of the second electromagnetic radiation part 132 or the first electromagnetic radiation part 130. Again, in one embodiment, when the fluid of interest is crude oil, and the crude oil is present in the multiphase fluid 12, the reflected portion 134 is around 3%-5% of the second electromagnetic radiation part 132 or the first electromagnetic radiation part 130. Again, in one embodiment, when the fluid of interest is water, and water is present in the multiphase fluid 12, the reflected portion 134 is around 5%-18% of the second electromagnetic radiation part 132 or the first electromagnetic radiation part 130. In still another embodiment, when the fluid of interest is natural gas, and natural gas is present in the multiphase fluid 12, the reflected portion 134 is about 20% to about 80% of the second electromagnetic radiation part 132 or the first electromagnetic radiation part 130.

The reflected portion 134 travels through the first electromagnetic guiding device 100 to the primary coupling device 108. As previously noted the primary coupling device 108 in one example is a 50:50 coupler, and therefore splits the reflected portion 134 into a first split reflected portion 136 and a second split reflected portion 138. In one embodiment, a processing subsystem (not shown) analyzes the multiphase fluid 12 (see FIG. 1) based upon the first split reflected portion 136 and the second electromagnetic radiation part 132. The processing subsystem, for example, may be coupled to the primary coupling device 108. In the presently contemplated configuration, considering that the primary coupling device 108 is a 50:50 coupler, and when there are no losses, the following condition is satisfied:

$$P_1 \sim P_2 \tag{1}$$

wherein $P_1$ is power in the first electromagnetic radiation part 130 and $P_2$ is power in the second electromagnetic radiation part 132.

Accordingly, it may be said that the processing subsystem (not shown) analyzes the multiphase fluid 12 (see FIG. 1) based upon the first split reflected portion 136, and the second electromagnetic radiation part 132 or the first electromagnetic radiation part 130 to generate analysis results of the multiphase fluid 12. The analysis results, for example, may include information about the presence or absence of a fluid of interest in the multiphase fluid 12, concentration of the fluid of interest in the multiphase fluid 12, phase fraction, natural gas to liquid phase fraction, remaining life of the conduit 14, or combinations thereof.

As shown in FIG. 2, in this embodiment, the first split reflected portion 136 is directed towards the detector 120 by the primary coupling device 108 via the third electromagnetic guiding device 112. In this embodiment, the primary coupling device 108 directs the second split reflected portion 138 towards the laser source 124 via the second electromagnetic guiding device 110. In one embodiment, the second split reflected portion 138 of the first electromagnetic radiation part 130 is discarded. In another embodiment, the second split reflected portion 138 may be used as part of a feedback system for the laser source 124.

The detector 120 receives the first split reflected portion 136. In the presently contemplated configuration, the first split reflected portion 136 and the second electromagnetic radiation part 132 are optical signals. Therefore, the detector 120 converts the first split reflected portion 136 and the second electromagnetic radiation part 132 into reflected electrical signals 140 and reference electrical signals 142, respectively. The reflected electrical signals 140 are representative of the first split reflected portion 136, and the reference electrical signals 142 are representative of the second electromagnetic radiation part 132.

Furthermore, the device 101 includes electronics and circuitry 144 that is coupled to the detector 120. The electronics and circuitry 144, for example, may be the processing subsystem (not shown) that analyzes the multiphase fluid 12 to generate the analysis results. In this embodiment, the electronics and circuitry 144 receives the reflected electrical signals 140 and the reference electrical signals 142 from the detector 120. In this embodiment, the electronics and circuitry 144 generates the signals 28 (see FIG. 1) that are representative of the analysis results of the multiphase fluid 12. As previously noted, the analysis results, for example, may include information about the presence or absence of the fluid of interest in the multiphase fluid 12, concentration of the fluid of interest in the multiphase fluid 12, natural gas to liquid phase fraction, remaining life of the conduit 14, or combinations thereof. As previously noted with reference to FIG. 1, the signals 28 are received by the computing and display device 30 (see FIG. 1).

According to one embodiment, the electronics and circuitry 144 includes a processing section including at least one processor, microprocessor, controller, general purpose processor of digital signal processor. The processing section in one example is used to process the data according to computer programs encoded with instructions. There can also be memory coupled to the processing section to store the computer programs, test results, analysis as well as historical data. Such processing can be done on the device 101 to obtain the desired results that are communicated to a display device or process/pre-process certain data for communication to the computing and display device. In a further embodiment, the electronics and circuitry include a communication section that is configured to transmit the signals and data to the computing and display device.

As previously noted, the device 101 is used in very harsh conditions. Therefore, the first electromagnetic guiding device 100 is covered by a tube 146. The electromagnetic guiding devices 100, 110, 112, in a non-limiting example, may have a diameter of around 300 micron, and length of about 2 meter. The electromagnetic guiding devices 100, 110, 112 may have a coating of carbon, hydrogen capturing gels, or the like to prevent formation of hydroxyl due to the presence of free hydrogen atoms inside the conduit 14 (see FIG. 1). Additionally, the first portion 18' of the device 101 is covered by the casing 106 to keep intact the components of the device 101 including components 100, 108, 110, 112, 120, 124, 144, of the device 101 in respective locations, and save the components from the harsh conditions.

Figure 3:
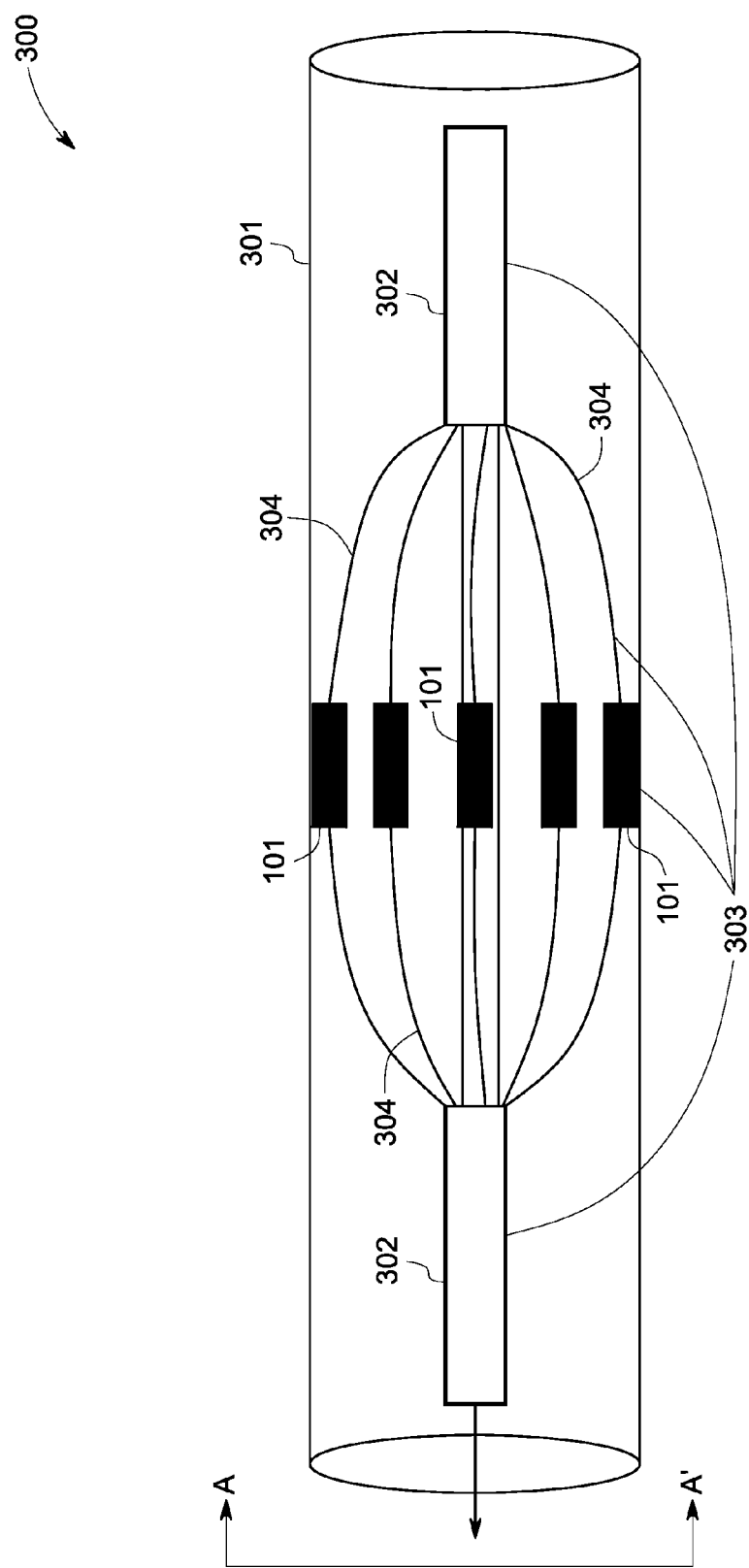
FIG. 3 is a side elevation view of an exemplary analysis system, in accordance with one aspect of the present systems.

Referring now to FIG. 3, a side elevation view of an exemplary analysis system 300 showing an instrument 303 inserted into a pipeline 301 of a conduit, in accordance with one aspect of the present systems. The instrument 303 is used for analyzing the multiphase fluid 12 (see FIG. 1), production logging techniques, and investigative logging techniques of the conduit. The instrument 303 includes one or more devices, such as, the device 16 (see FIG. 1) and the device 101 (see FIG. 2).

As shown in FIG. 3, the instrument 303 includes a central rod or mandrel 302 for connection with a down-hole tool string (not shown). A plurality of devices or probes are mounted on the mandrel 302 by a respective bow string 304. In the presently contemplated configuration, one or more of the devices 101 (see FIG. 2) are mounted on the mandrel 302. While in the presently contemplated configuration, twelve of the devices 101 are mounted on the mandrel 302, in certain embodiments, a desired number of the devices 101 may be mounted on the mandrel 302. While in the presently contemplated configuration, similar devices 101 are mounted on the mandrel 302, in certain embodiments different types of probes or devices may be mounted on the mandrel 302. In one embodiment, other devices along with one or more of the devices 16 may be mounted on the mandrel 302. It is further noted that while the presently contemplated configuration shows employment of the device 101 in the instrument 303, in certain embodiments, the device 101 may be independently used. In one embodiment, the bow springs 304 are mounted around the circumference of the mandrel 302 so that the devices 101 form a circular array that follows the periphery of the pipeline 301 of a conduit, such as the conduit 14 (see FIG. 1).

Figure 4A:
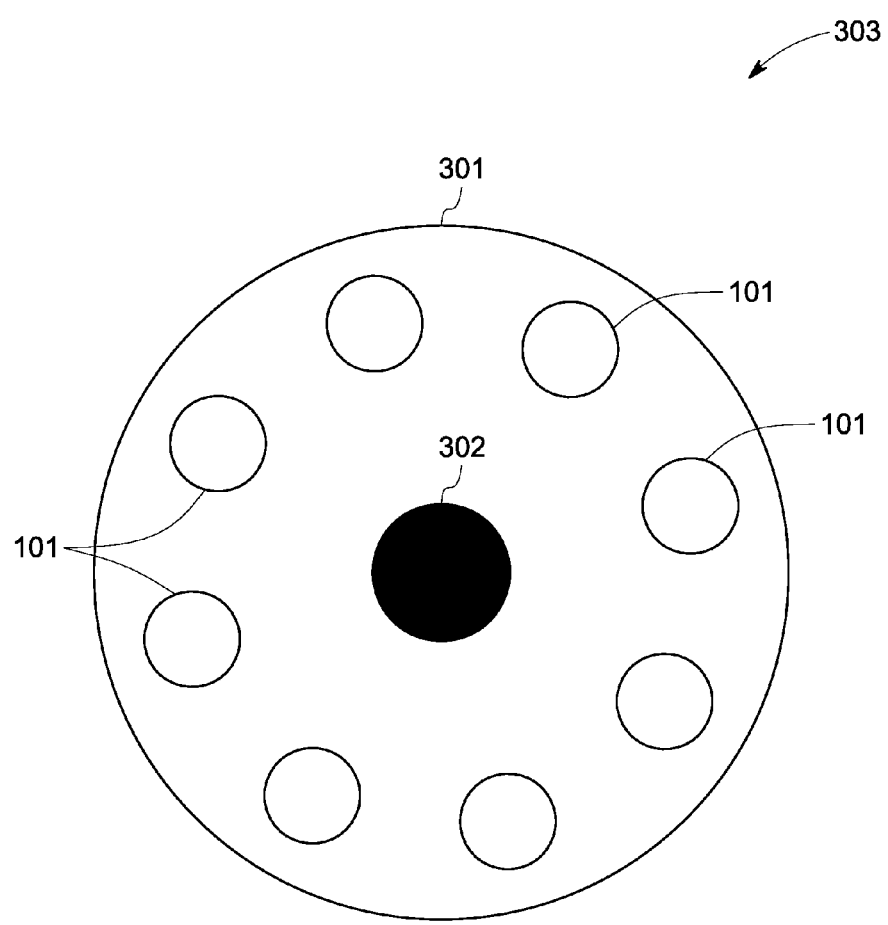
FIG. 4(a) is a cross-sectional view of the instrument referred to in FIG. 3 when viewed from a direction AA', in accordance with one aspect of the present systems.
Figure 4B:
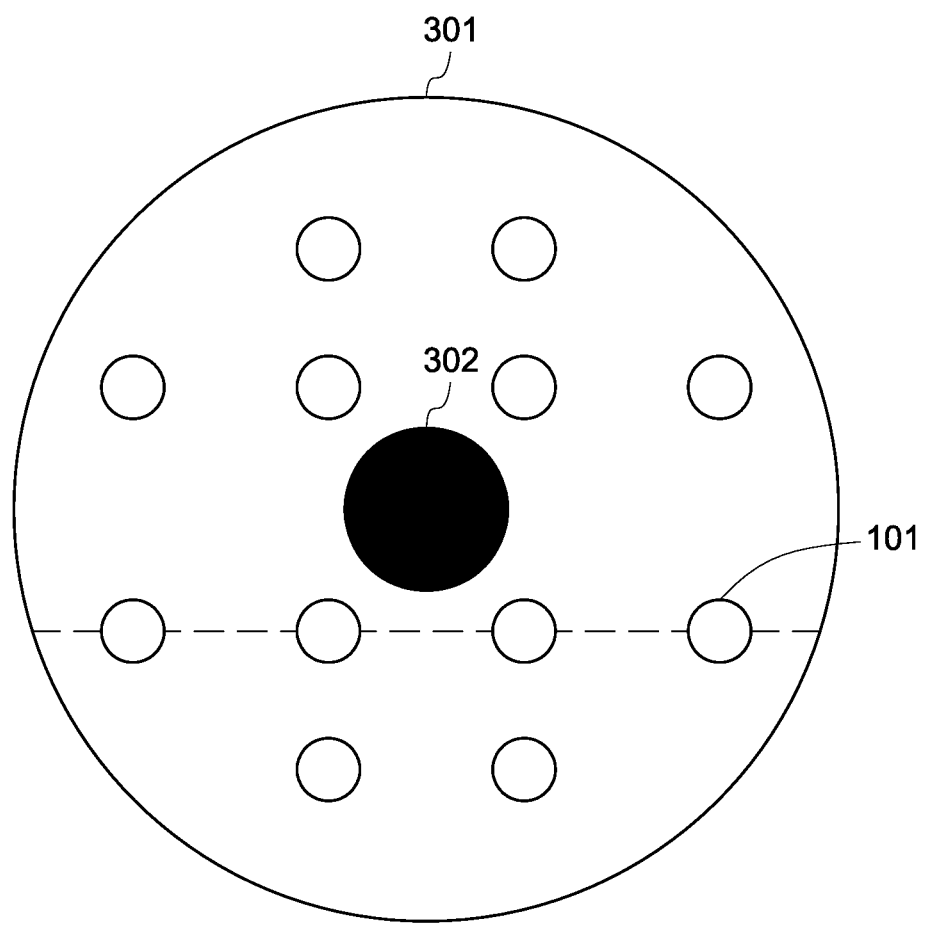
FIG. 4(b) is a cross-sectional view of an instrument that has devices arranged in a matrix form around a mandrel, in accordance with one aspect of the present systems.
Figure 4C:
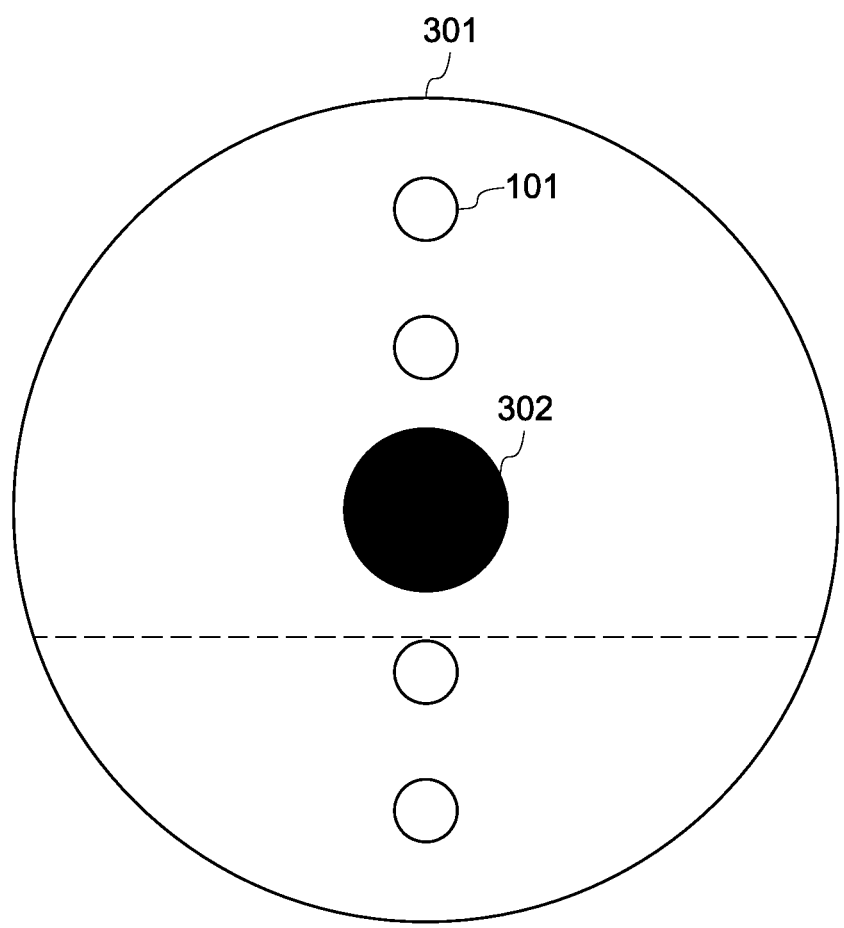
FIG. 4(c) is a cross-sectional view of an instrument that has devices arranged in a linear manner, in accordance with one aspect of the present systems.

FIG. 4(a) is a cross-sectional view of the instrument 303 when viewed from a direction AA' from FIG. 3. As shown in FIG. 4(a), the devices 101 are arranged to form a circular array that follows the pipeline 301. In certain embodiments, the devices 101 and/or probes may be arranged in a matrix form around the mandrel 302. FIG. 4(b) is a cross-sectional view of an instrument that has the devices 101 arranged in a matrix form around the mandrel 302. In alternative embodiments, the devices 101 and/or probes may be arranged linearly around the mandrel 302. FIG. 4(c) is a cross-sectional view of an array tool wherein the devices 101 are arranged in a linear manner. In certain embodiments, when one or more of the devices 101 are used in an instrument, one or more reference coupling devices and one or more references detectors may be installed in one or more of the devices 101 to reduce errors and normalize manufacturing differences in the laser sources in the plurality of devices 101.

Figure 7A:
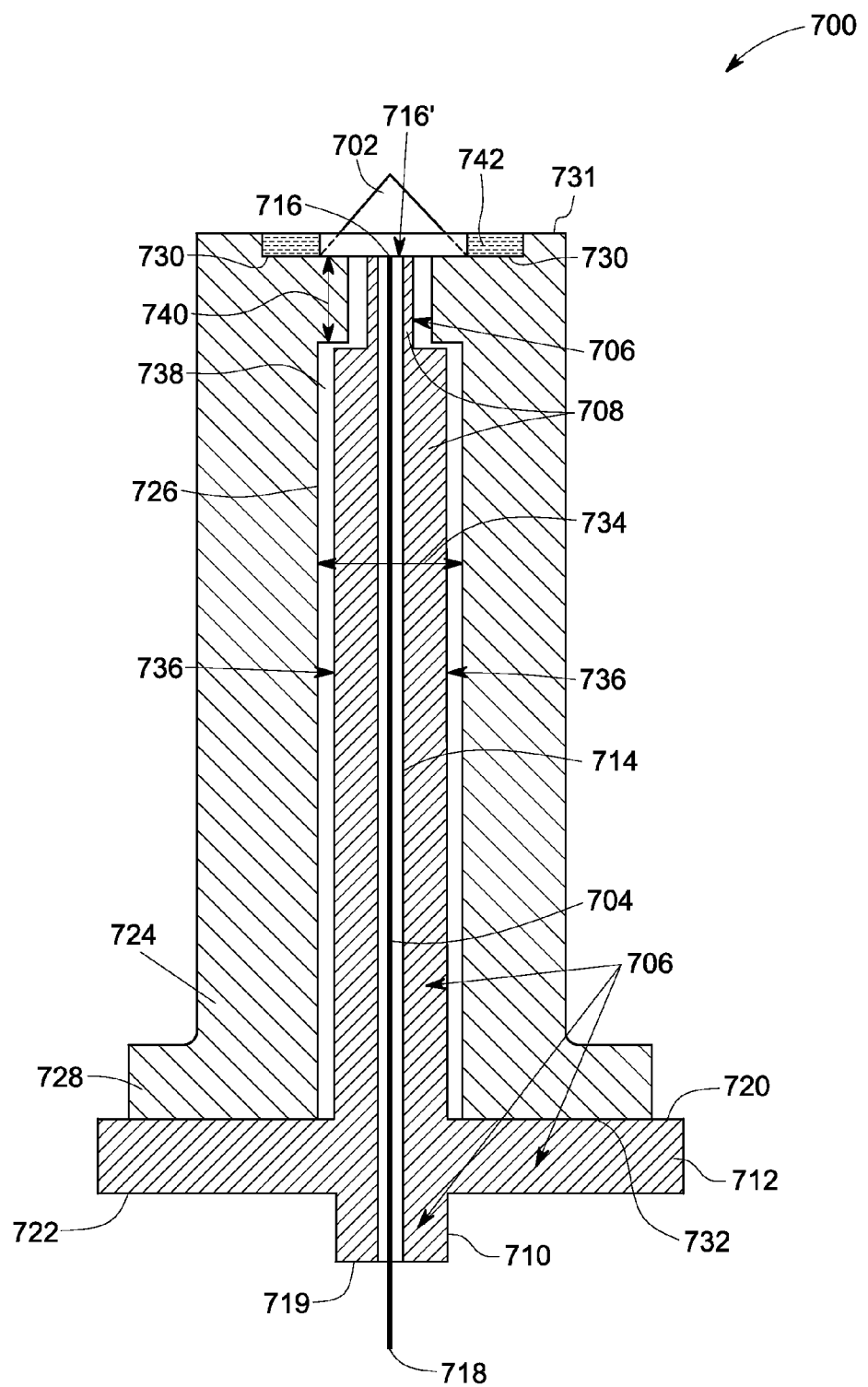
FIG. 7(a) is a longitudinal cross-section view of a holding device that holds a reflector and an electromagnetic guiding device, in accordance with one aspect of the present techniques.

FIG. 7(a) is a longitudinal cross-sectional view of a holding device 700 that holds a reflector 702 and an electromagnetic guiding device 704 to align a principal optical axis of the reflector 702 and a principal optical axis of the electromagnetic guiding device 704, in accordance with one aspect of the present system. It is noted that FIG. 7(*a*) is oriented with the reflector 20 on the top as compared to FIG. 1 or FIG. 2. Furthermore, the holding device 700 maintains a physical contact between the reflector 702 and the electromagnetic guiding device 704. As used in this example, the electromagnetic guiding device 704 is located along the entire length of the holding device 700. Additionally, the holding device 700 permanently holds the reflector 702, such that, the reflector 702 does not dislocate or move during usage. The reflector 702, for example, may be the reflector 20 (see FIG. 1 and FIG. 2). The electromagnetic guiding device 704, for example, may be at least a portion of the electromagnetic guiding device 19, the second portion 21 of the electromagnetic guiding device 19 (see FIG. 1) or the first electromagnetic guiding device 100 (see FIG. 2).

In the presently contemplated configuration, the holding device 700 is approximately cylindrical in shape. An exemplary top view of the holding device 700 that shows a circular top view of the holding device 700 due to the cylindrical shape of the holding device 700 is shown in 7(*b*). As shown in FIG. 7(*a*), the holding device 700 includes a male connector 706. The male connector 706 includes a first male extension 708, a second male extension 710, and a male central disk 712. In the presently contemplated configuration, the first male extension 708, the second male extension 710 and the male central disk 712 together form the structure of the male connector 706. In one embodiment, a first male extension 708, a second male extension 710, and a male central disk 712 form the structure of the male connector 706 without one or more joints.

As shown in the presently contemplated configuration, the male central disk 712 is circular in shape. Furthermore, the male central disk 712 has a diameter larger than the diameter of the first male extension 708, and the diameter of the second male extension 710. The male central disk 712 has a top surface 720 and a bottom surface 722. In one embodiment, the top surface 720 and the bottom surface 722 are substantially flat or planar. In one embodiment, edges of the top surface 720 and edges of the bottom surface 722 are curved. As shown in FIG. 7(*a*), the first male extension 708 extends from the top surface 720 of the male central disk 712 and the second male extension 710 extends from the bottom surface 722. Accordingly, the first male extension 708 and the second male extension 710 extend from opposite surfaces 720, 722 of the male central disk 712.

In the presently contemplated configuration, the first male extension 708 and the second male extension 710 are substantially cylindrical rod shaped structures. As shown in FIG. 7(*a*), the length of the first male extension 708 is greater than the length of the second male extension 710. In this embodiment, the male connector 706 does not have joints between the first male extension 708, the second male extension 710, and the male central disk 712. Furthermore, the male connector 706 has a central hole 714 that continuously passes through the center of the first male extension 708, the center of the male central disc 712 and the center of the second male extension 710.

As shown in FIG. 7(*a*), the electromagnetic guiding device 704 passes through the central hole 714. A first end 716 of the electromagnetic guiding device 704 ends at a first edge 716' of the male connector 706 or a first edge 716' of the first male extension 708, and a second end 718 of the electromagnetic guiding device 704 may go beyond a second edge 719 of the male connector 706. The second end 718 of the electromagnetic guiding device 704, for example, may be connected to a female connector (not shown) via the second male extension 710. The diameter of the central hole 714 is equal or minimally bigger than the diameter of the electromagnetic guiding device 704. For example, when the diameter of the electromagnetic guiding device 704 is about 280 microns, the diameter of the central hole 714 is about 282 microns.

Furthermore, the holding device 700 has a holder 724. The holder 724 covers the first male extension 708 to hold the reflector 702, and maintain a physical contact between the first end 716 of the electromagnetic guiding device 704 and the reflector 702. As shown in FIG. 7(*a*), the holder 724 has a holder hole 726 and a holder central disk 728. In the presently contemplated configuration, the holder 724 further comprises a depression 730 on a top surface 731 of the holder 724. In the presently contemplated configuration the depression 730 is circular in shape, and has a diameter smaller than the diameter of the top surface 731 of the holder 724.

Figure 8:
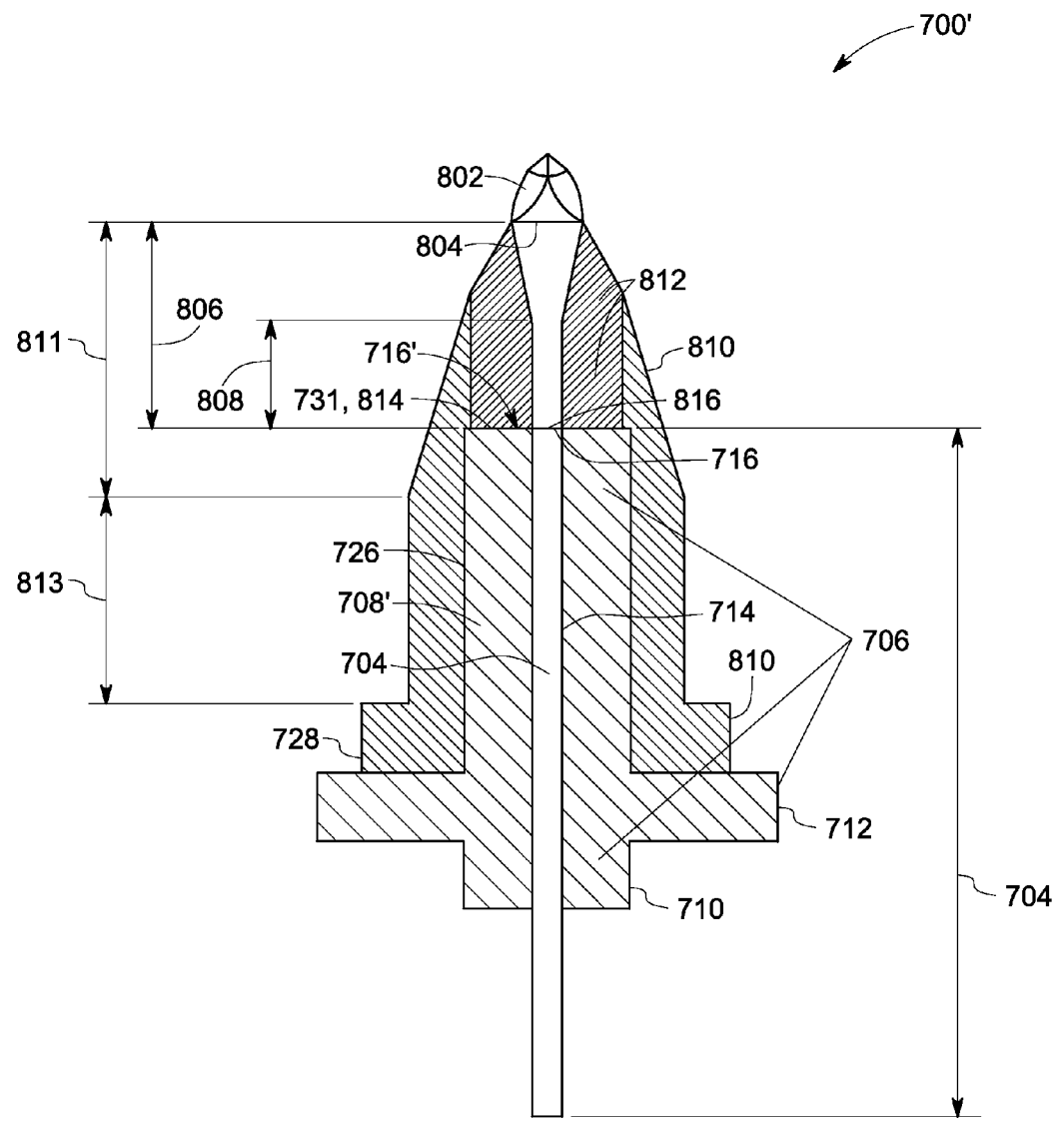
FIG. 8 is a longitudinal cross-section view of a holding device that holds a reflector and an electromagnetic guiding device, in accordance with another aspect of the present techniques.

In this embodiment, the holder 724 is cylindrical in shape. In certain embodiments, the holder 724 may be a tapered cylinder or a combination of a cylinder and a tapered cylinder. An exemplary holder that has a shape which is a combination of a cylinder and a tapered cylinder is shown in FIG. 8. However, the holder 724 may have other shapes depending upon the application. The holder hole 726 has a shape based upon the shape of the first male extension 708 to allow the first male extension 708 inside the holder hole 726. For example, in the presently contemplated configuration, the first male extension 708 and the holder hole 726 are cylindrical in shape. In one embodiment, the holder hole 726 has a shape and size such that when the first male extension 708 is inserted into the holder hole 726, the outer surface of the first male extension 708 substantially touches the inner surface of the holder hole 726. In one embodiment, the holder hole 726 has a shape and size such that when the first male extension 708 is inserted into the holder hole 726, an equal distance is maintained between the outer surface of the first male extension 708 and the inner surface of the holder hole 726. In one embodiment, the holder hole 726 has a shape and size such that when the first male extension 708 is inserted into the holder hole 726, the first male extension 708 gets locked, such as by friction fit, with the holder hole 726. In one embodiment, the holder hole 726 and/or the first male extension 708 may have one or more provisions for locking the first male extension 708 with the holder hole 726. In the presently contemplated configuration, a length of the first male extension 708 is slightly less than a length of the holder 724.

In one embodiment, a bottom surface 732 of the holder disk 728 and the top surface 720 of the male disk 712 may have a mechanism or provision that locks the holder disk 728 and the male central disk 712 together. Accordingly, in such embodiment, the first male extension 708 is inserted into the holder hole 726 of the holder 724 till the bottom surface 732 of the holder disk 728 gets locked with the top surface 720 of the male central disk 712. In one embodiment, a bottom surface 732 of the holder disk 728 may be soldered with the top surface 720 of the male central disk 712. Since in this embodiment, the length of the first male extension 708 is slightly less than the length of the holder 724, the first edge 716' of the male connector 706 is substantially aligned with the depression 730 of the holder 724. In the presently contemplated configuration, an inner diameter 734 of the holder hole 726 is slightly larger than an outer diameter 736 of the first male extension 708 of the male connector 706. Since the inner diameter 734 of the holder hole 726 is slightly larger than the outer diameter 736 of the first male extension 708, a space 738 is left between the first male extension 708 and the holder hole 726. In the presently contemplated configuration, a diameter of the holder disk 728 is smaller than a diameter of the male central disk 712. However, in alternative embodiments, the diameter of the holder disk 728 may be bigger or equal to the diameter of the male central disk 712.

Furthermore, in certain embodiments, a determined length 740 of the first male extension 708 and the holder hole 726 may have narrower diameters in comparison to diameters of the rest of the length of the first male extension 708 and the holder hole 726. For example, a determined length 740 of the first male extension 708 and the holder hole 726 may have a diameter D, when the diameter of the rest of the length of the first male extension 708 and the holder hole 726 is D+5. It is noted that in the presently contemplated configuration, the determined length 740 has a constant diameter.

Furthermore, as previously noted, the holder 724 has the depression 730. In this embodiment, the depression 730 is circular in shape, and a diameter of the depression 730 is smaller than a diameter of the holding device 724. The reflector 702 is placed in the depression 730 of the holder 724, and a glass preform 742 is formed in space left in the depression 730 after placement of the reflector 702 in the depression 730. The glass preform 742, for example, may be a glass to metal sealing, or the like. The glass preform 742 covers an entire area of the depression 730 except an area in the depression 730 that is covered by the base of the reflector 702. The glass preform 742, for example, has an internal shape and an external shape. The internal shape depends upon a shape of a base of the reflector 702, and the external shape depends upon the shape of the depression 742. Exemplary internal shapes and an external shape is shown with reference to FIG. 9 and FIG. 10. Due to a thickness T of the glass preform 742, a height of external surfaces of a reflector placed or located in the glass preform 742 is covered by the glass preform 742. The height of the external surfaces covered by the glass preform 742, for example is less than or equal to the thickness of the glass preform 742.

As previously noted, the reflector 702 is in a direct physical contact with the multiphase fluid of the conduit 14 (see FIG. 1). Additionally, the conduit 14 has very harsh conditions. Therefore, the glass preform 742 is made of one or more materials or made using one or more technologies that are capable of sustaining the harsh conditions of the conduit 14 (see FIG. 1), and maintaining the position of the reflector 702.

In certain applications, a stagnant position of the reflector 702 with respect to the position of the electromagnetic guiding device 704 is desirable for maintaining an alignment of the principal optical axis of the reflector 702 and the principal optical axis of the electromagnetic guiding device 704. The glass preform 742 sustains the position of the reflector 702 to maintain the alignment of the principal optical axis of the reflector 702 and the principal optical axis of the electromagnetic guiding device 704. The holding device 700 aligns and maintains the alignment of the principal optical axis of the electromagnetic guiding device 704 and the principal optical axis of reflector 702. In the presently contemplated configuration, the holding device 700 has a shape that is resilient to complex flows of the multiphase fluid 12 in the reservoir 14.

Figure 7B:
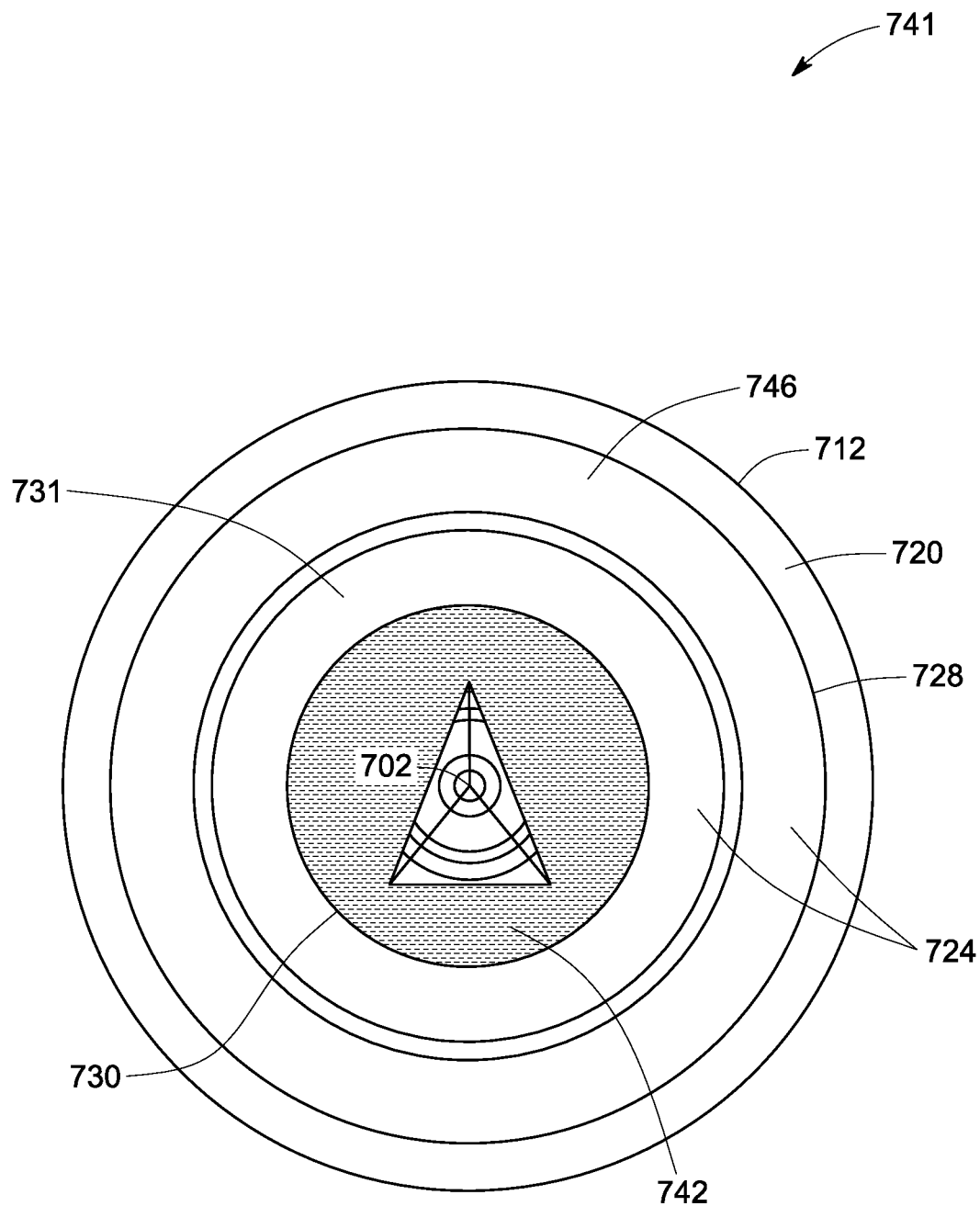
FIG. 7(b) is a top view of the holding device shown in FIG. 7(a), in accordance with one aspect of the present systems.

FIG. 7(b) is a top view 741 of the holding device 700 shown in FIG. 7(a), in accordance with one aspect of the present systems. As shown in FIG. 7(b), the reflector 702 is placed in the depression 730 (also shown in FIG. 7(a)) of the holder 724. Furthermore, the reflector 702 is fixed at a location in the depression 730 by application of the glass preform 742. FIG. 7(b) shows the top surface 731 of the holder 724 and a portion of a top surface 746 of the holder disk 728. Additionally, 7(b) shows the top surface 720 (see FIG. 7(a)) of the male central disk 712.

FIG. 8 depicts a longitudinal cross-sectional view of a holding device 700' for holding a reflector 802 and the electromagnetic guiding device 704, in accordance with another aspect of the present systems. The holding device 700' is another embodiment of the holding device 700 shown in FIG. 7(a). Same reference numerals are used for similar components in the holding device 700 (see FIG. 7(a)) and the holding device 700'. The reflector 802, for example, includes a retroreflector, a corner cube reflector, a chamfered corner cube reflector, a corner cube prism, a chamfered corner cube prism, a corner cube retroreflector, a chamfered corner cube retroreflector, a lens, or a cone. The reflector 802, for example, may be the reflector 20 (see FIG. 1), or the reflector 702. In the presently contemplated configuration, the reflector 802 has an extension 806 extending out from a hypothetical base 804 of the reflector 802. As used herein, the term "hypothetical base" is used to refer to a base of a reflector that would have existed without an extension that extends out of the hypothetical base.

For example, when the reflector 802 is a chamfered corner cube reflector, the hypothetical base 804 is a circular base without an extension. Similarly, when the reflector 802 is a corner cube prism, the hypothetical base 804 is a triangular base without an extension. In the presently contemplated configuration, the reflector 802 is a chamfered corner cube retroreflector; therefore, the hypothetical base 804 is circular in shape. A shape of the extension 806, for example, may be circular, cylindrical, rod shaped, triangular, tapered-cylindrical, conical, or combinations thereof. The reflector 802 and the extension 806 are made of same material. The reflector 802 and the extension 806 may be a single structure without joints or may have one or more joints to form a single structure. As shown in the presently contemplated configuration, the extension 806 has a larger diameter near the hypothetical base 804, and gradually reduces to form a rod shaped structure 808.

Furthermore, as shown in the FIG. 8, the holding device 700' includes the male connector 706 (see FIG. 7(a)). The male connector 706 includes a first male extension 708', the second male extension 710, and the male central disk 712. (See FIG. 7(a)). It is noted that in this embodiment, the first male extension 708' has a constant diameter across respective length in comparison to the first male extension 708 in FIG. 7(a) where the diameter of the determined length 740 of the first male extension 708 is lesser than the rest of the first male extension 708. Additionally, as previously noted with reference to FIG. 7(a), the electromagnetic guiding device 704 passes through the central hole 714 that passes through the first male extension 708, the male central disk 712, and the second male extension 710. The holding device 700' includes a holder 810 that is similar to the holder 724 referred to in FIG. 7(a) with few differences. In the presently contemplated configuration, the holder 810 has a semi-cylindrical shape, and a semi tapered-cylindrical shape.

As shown in FIG. 8, a shape of bottom portion 813 of the holder 810 is cylindrical, and a shape of top portion 811 of the holder 810 is tapered-cylindrical. The holder 810 includes the holder hole 726 and the holder central disk 728. In the presently contemplated configuration, a length of the first male extension 714 is lesser than a length of the holder 810. Therefore, unlike the embodiment shown with reference to FIG. 7(a), the top surface 716' (see FIG. 7(a)) of the male connector 706 does not reach the top surface 731 (see FIG. 7(a)) of the holder 810.

The holding device 700' further includes a reflector holder 812. The reflector holder 812, for example, may be cylindrical, tapered-cylindrical, or a combination thereof. In one embodiment, the shape of the reflector holder 812 may depend upon a shape of the holder 810. For example, when a top portion of the holder 810 is cylindrical, the reflector holder 810 may be cylindrical. In the presently, contemplated configuration, the top portion of the holder 810 is tapered-cylindrical, therefore, a top portion of the reflector holder 810 is tapered-cylindrical. Additionally, as shown in FIG. 8, a bottom portion of the reflector holder 812 may be cylindrical. In one embodiment, a diameter of a bottom surface 814 of the reflector holder 812 is substantially similar to a diameter of the top surface 716' of the male connector 706. The reflector holder 812, for example, is hollow. The reflector holder 812 receives the extension 806 of the reflector 802 such that the reflector 802 is outside the reflector holder 812. The reflector 802 is placed in the reflector holder 812 such that at least a portion of the extension 806 goes inside the hollow reflector holder 812.

The reflector holder 812 with the reflector 802 is placed on the top surface 716' of the male connector 706. In this embodiment, the diameter of the top surface 716' of the first male extension 708 is similar to the diameter of a bottom surface 814 of the reflector holder 812. Subsequently, the first male extension 708, the reflector holder 812, and the reflector 802 are received by the holder hole 726 of holder 810 such that the reflector 802 is outside the holder hole 726. Accordingly, the holder 810 covers the reflector holder 812 and the first male extension 708.

According to one embodiment, a mechanism is applied to the reflector 802, the reflector holder 812, the holder 810, and the top surface 716' of the first male extension 708 that joins or bonds the bottom surface 814 of the reflector holder to the top surface 716' of the first male extension 708 to align a principal optical axis of the reflector 802 with a principal optical axis of the electromagnetic guiding device 704. Furthermore, the mechanism makes a physical contact between the first end 716 of the electromagnetic guiding device 704 and a base 816 of the extension 806. The mechanism further fills in a remaining hollow space left in the reflector holder 812. Additionally, the mechanism permanently fixes the position of the reflector 802 with respect to the position of the holding device 700'. The mechanism, for example, includes gold blazing.

Figure 5:
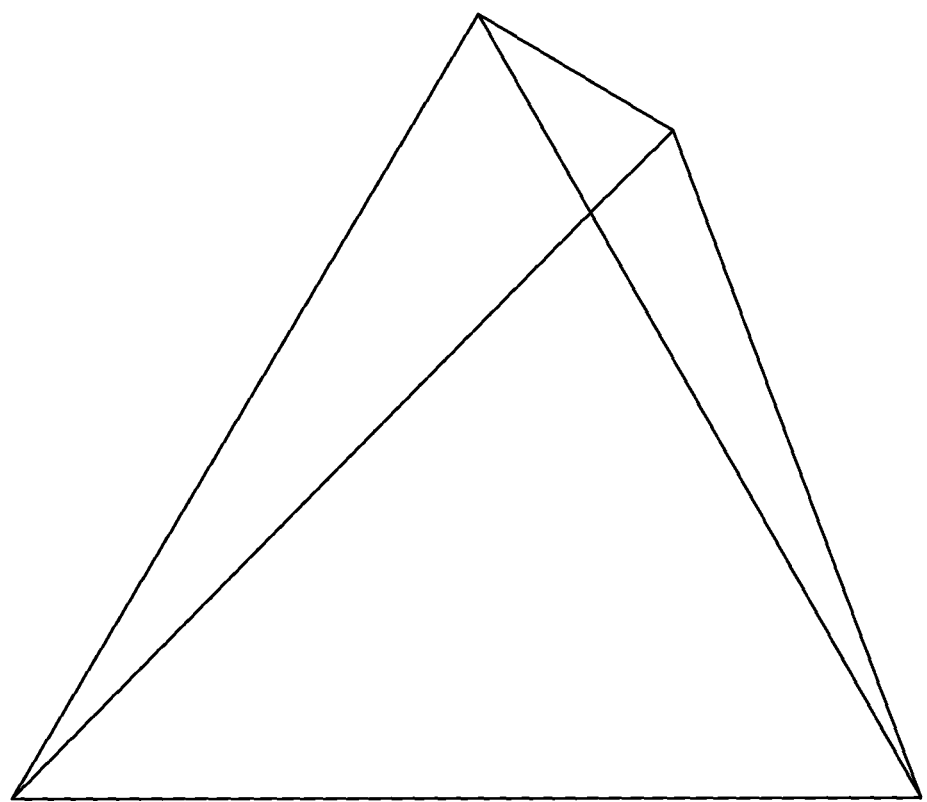
FIG. 5 is a side elevation view of a corner cube retroreflector, in accordance with one aspect of the present systems.
Figure 6:
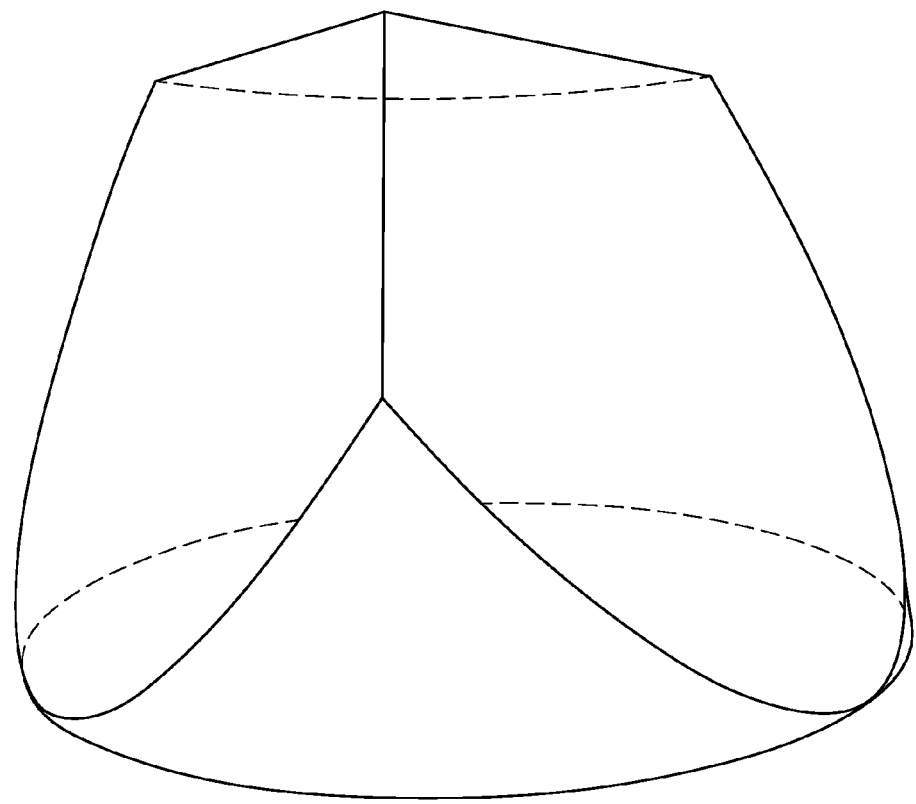
FIG. 6 is a side elevation view of a chamfered corner cube retroreflector, in accordance with one aspect of the present systems.
Figure 9:
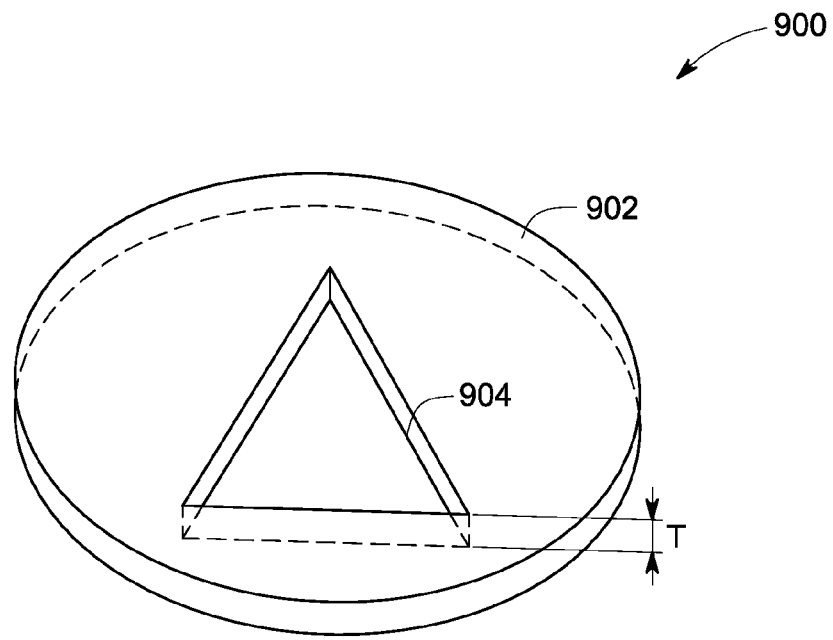
FIG. 9 is an exemplary glass preform, in accordance with one embodiment of the present systems.

Turning now to FIG. 9 along with FIG. 7(a), an exemplary glass preform 900 is shown, in accordance with one embodiment of the present system. The glass preform 900 has an external shape 902 and an internal shape 904. The glass preform 900, for example, is similar to the glass preform 742 (see FIG. 7(a)). In this example, the external shape 902 is circular, and the internal shape 904 is triangular. When the depression 730 is circular in shape, the external shape 902 of the glass preform 900 is circular. Furthermore, when the shape of a base of a reflector located 702 (not shown in FIG. 9) is triangular (e.g. base of the corner cube reflector in FIG. 5 is triangular), the internal shape 904 of the glass preform 900 is triangular. Furthermore, the glass preform 900 has a thickness T. Due to the thickness T of the glass preform 900, a height of external surfaces of a reflector placed or located in the glass preform 900 is covered by the glass preform 900. The height of the external surfaces covered by the glass preform 900, for example is less than or equal to the thickness of the glass preform 742.

Figure 10:
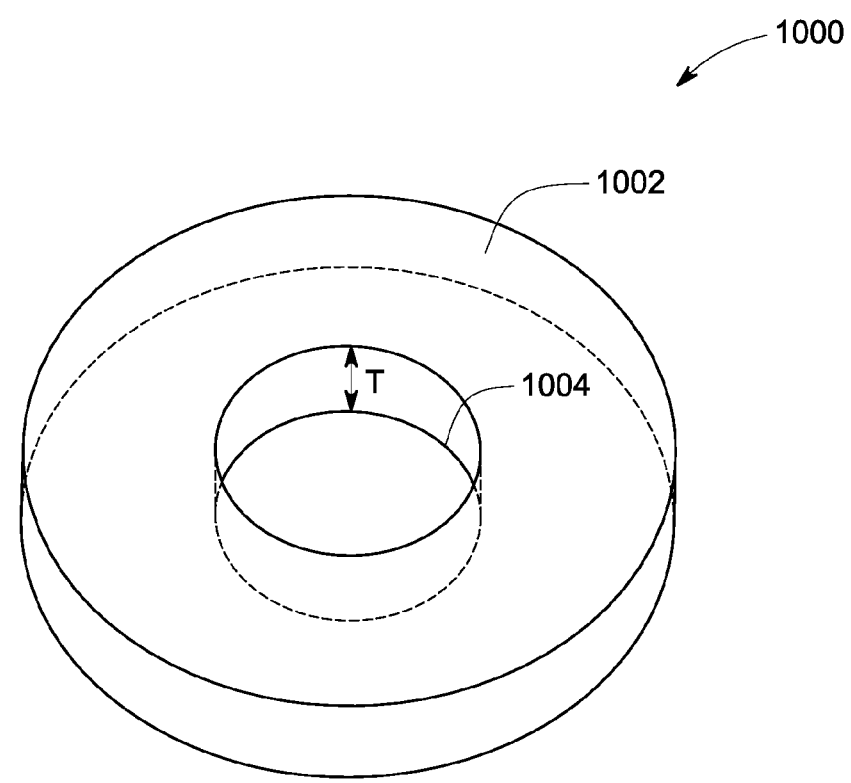
FIG. 10 is an exemplary glass preform, in accordance with another embodiment of the present systems.

Referring now to FIG. 10, an exemplary glass preform 1000 is shown, in accordance with one embodiment of the present system. The glass preform 1000 in this example has an external shape 1002 and an internal shape 1004. As shown in FIG. 10, the external shape 1002 of the glass preform 1000 is circular which fits in the circular depression 742 (see FIG. 7(a)). Furthermore, the internal shape 1004 is circular that fits a circular base of a chamfered corner cube retroreflector. For example, the internal shape 1004 of the glass preform 1000 fits the circular base of the chamfered corner cube retroreflector referred to in FIG. 6. Again, the glass preform 1000 has a thickness T.

Figure 11:
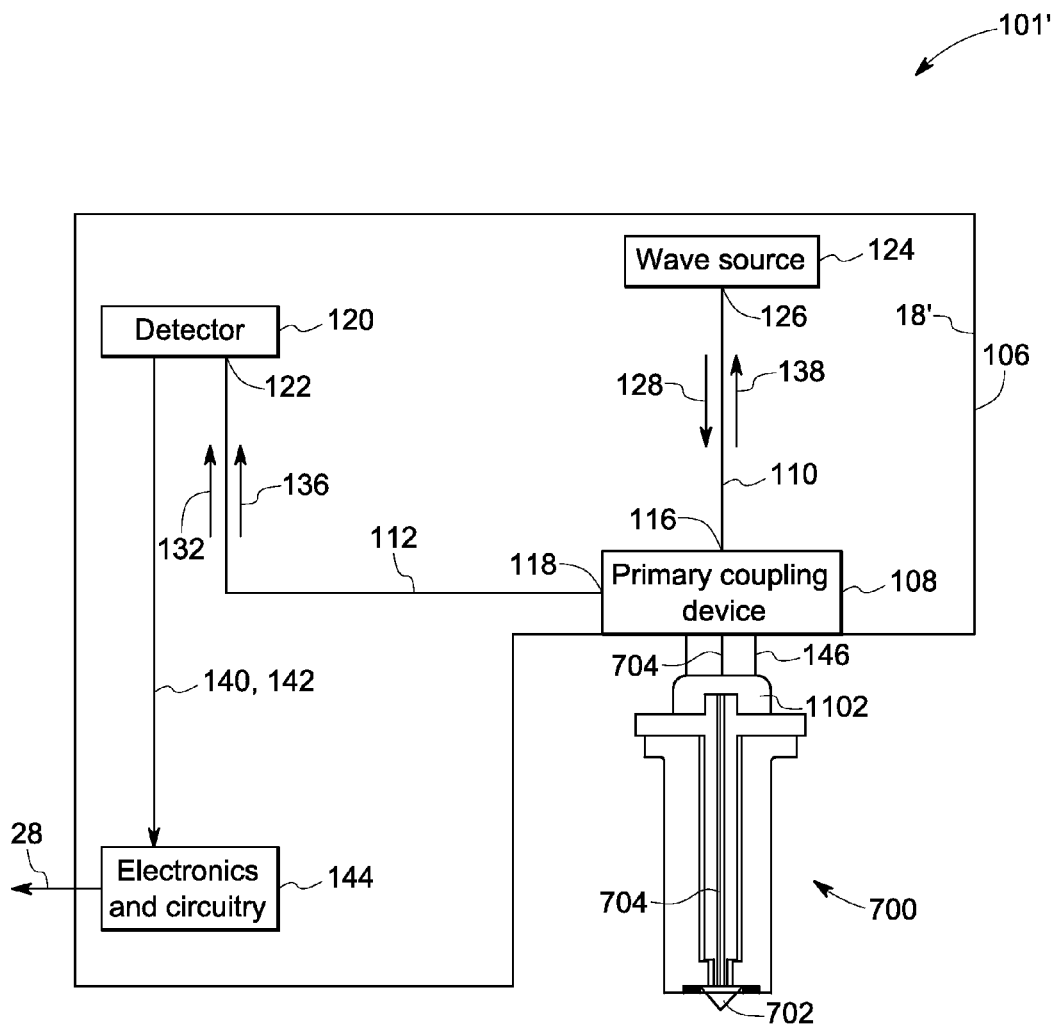
FIG. 11 is a diagrammatic illustration of the system (referred to in FIG. 2) that uses the holding device referred to in FIG. 7(a) and FIG. 7(b), in accordance with certain aspects of the present systems.

FIG. 11 is a system block diagram of a device 101' that uses the holding device 700 referred to in FIG. 7(a) and FIG. 7(b), in accordance with certain aspects of the present systems. Particularly, the block diagram shows the device 101' that is similar to the device 101 (see FIG. 2) except that the device 101' uses the holding device 700 to permanently hold the reflector 702, and align principal axes of the reflector 702 and the electromagnetic guiding device 704 (see FIG. 7(a)). It is further noted that in this embodiment, the electromagnetic guiding device 702 is used unlike the device 101 (see FIG. 2) that includes the first electromagnetic guiding device 100 (see FIG. 2). As shown in FIG. 7(b), the holding device 700 is coupled to a female connector 1102. Furthermore, the female connector 1102 is coupled to the primary coupling device 108 (see FIG. 2).

Figure 12:
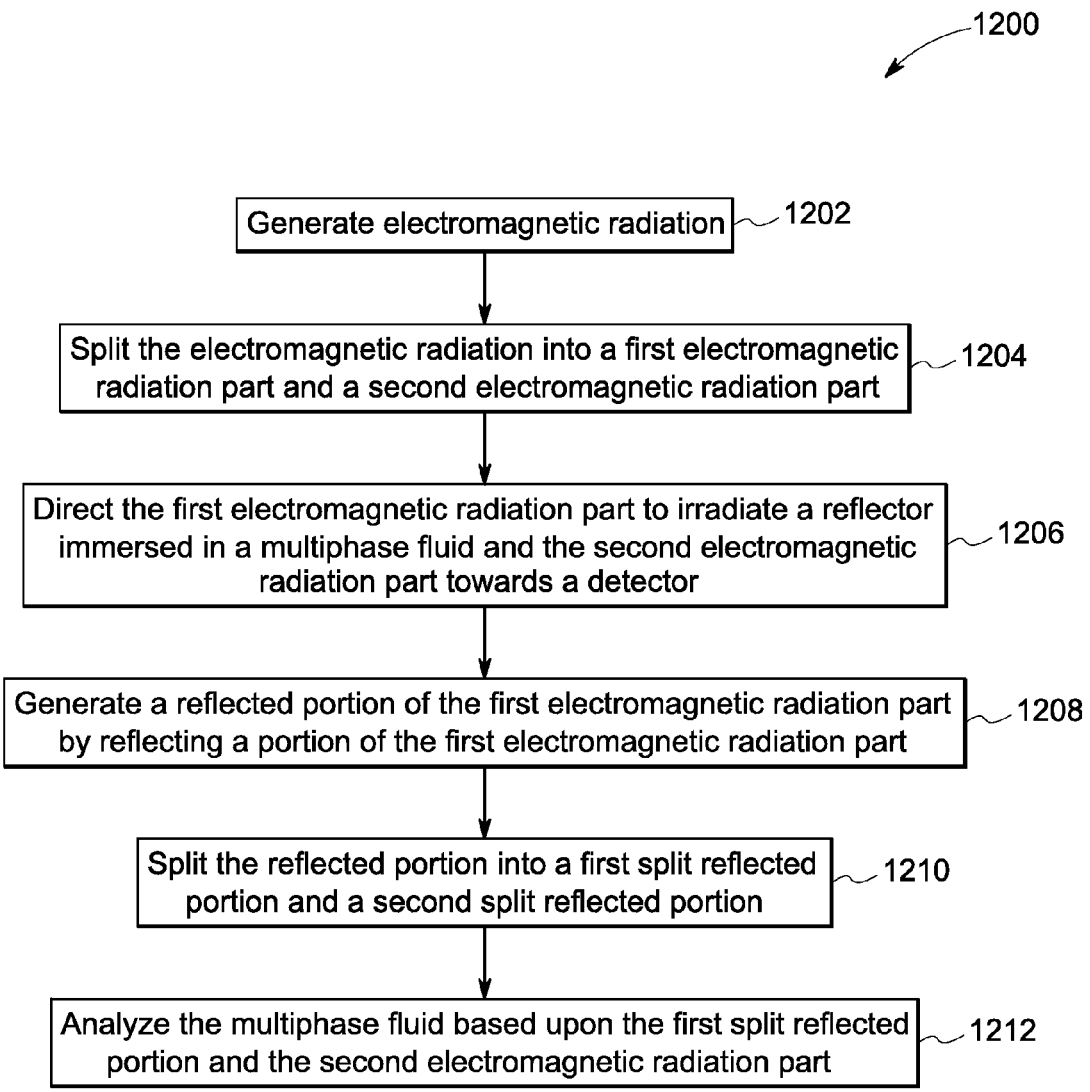
FIG. 12 is a flow chart that illustrates an exemplary method for analysis of a multiphase fluid, in accordance with another embodiment of the present techniques.

FIG. 12 is a flow chart that illustrates an exemplary method 1200 for analysis of a multiphase fluid, in accordance with one embodiment of the present techniques. At block 1202, electromagnetic radiation is generated. The electromagnetic radiation, for example, may be generated by the laser source 124 (see FIG. 2). The electromagnetic radiation, for example, may be the electromagnetic radiation 24 referred to in FIG. 1, or the electromagnetic radiation 128 referred to in FIG. 2. Furthermore, at block 1204 the electromagnetic radiation is split into two parts including a first electromagnetic radiation part and a second electromagnetic radiation part. In one embodiment, the electromagnetic radiation is split into two substantially equal parts. The electromagnetic radiation, for example, may be split by the primary coupling device 108 (see FIG. 2). The first electromagnetic radiation part, for example is the first electromagnetic radiation part 130, and the second electromagnetic radiation part, for example, is the second electromagnetic radiation part 132 (see FIG. 2).

At block 1206, the first electromagnetic radiation part is irradiated into a reflector that is fully immersed in the multiphase fluid. The reflector, for example, is the reflector 20 (see FIG. 1 and FIG. 2), or the reflector 702 (see FIG. 7(a) and FIG. 7(b). Additionally at block 1206, the second electromagnetic radiation part is directed towards a detector. The detector, for example, may be the detector 120 (see FIG. 2). At block 1208, a reflected portion of the first electromagnetic radiation part is generated. The reflected portion is generated due to reflection of a portion of the first electromagnetic radiation part by the reflector. Hereinafter "portion of the first electromagnetic radiation part" shall be referred to as "reflected portion of the first electromagnetic radiation part.

At block 1210, the reflected portion of the first electromagnetic radiation part is split in to two parts including a first split reflected portion and a second split reflected portion. In one embodiment, the reflected portion of the first electromagnetic radiation part is split into two substantially equal parts. The first split reflected portion, for example, may be the first split reflected portion 136 (see FIG. 2), and the second split reflected portion, for example, may be the second split reflected portion 138 (see FIG. 2). The reflected portion of the first electromagnetic radiation part, for example, may be split by the primary coupling device 108 (see FIG. 2). Subsequently at step 1212, the multiphase fluid may be analyzed to generate analysis results. The multiphase fluid, for example may be analyzed based upon the first split reflected portion and the second electromagnetic radiation part. The analysis results, for example, may include information about the presence or absence of a fluid of interest in the multiphase fluid, concentration of the fluid of interest in the multiphase fluid, phase fraction, natural gas to liquid phase fraction, remaining life of a conduit, or combinations thereof. In certain embodiment, the first split reflected portion may be converted into reflected electrical signals, and the second electromagnetic radiation part may be converted into reference electrical signals by the detector. Subsequently, the multiphase fluid may be analyzed based upon the reflected electrical signals and the reference electrical signals.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A holding device, comprising:
   a male connector comprising a first male extension and a second male extension that extend out of opposite surfaces of a male central disk;
   an electromagnetic guiding device continuously passing through a central hole that continuously passes through the first male extension, the male central disk and the second male extension;
   a reflector that is in a direct physical contact with a first end of the electromagnetic guiding device that ends at a top surface of the first male extension;
   a holder that covers the first male extension to hold the reflector, and maintain the physical contact between the first end of the electromagnetic guiding device and the reflector, and
   a reflector holder that receives an extension extending out from a hypothetical base of the reflector such that the reflector is outside the reflector holder.

2. The holding device of claim 1, wherein the first male extension and the second male extension are substantially rod shaped solid structures.

3. The holding device of claim 1, wherein the holder comprises a holder hole that receives the first male extension inside the holder hole.

4. The holding device of claim 1, wherein the holder hole has a shape based upon a shape of the first male extension.

5. The holding device of claim 1, wherein the holder comprises a holder disk that locks or sticks with the male central disk of the male connector.

6. The holding device of claim 5, wherein a bottom surface of the holder disk is soldered with a top surface of the male central disk.

7. The holding device of claim 1, wherein the shape of the holder is cylindrical, tapered cylindrical, or a combination of cylindrical and tapered cylindrical.

8. The holding device of claim 1, wherein the reflector comprises a retroreflector, a corner cube reflector, a chamfered corner cube reflector, a corner cube prism, a chamfered corner cube prism, a corner cube retroreflector, a chamfered corner cube retroreflector, a lens, or a cone.

9. The holding device of claim 1, wherein the reflector and the extension are made of same material.

10. The device of claim 1, wherein the reflector and the extension forms a single continuous structure without joints.

11. The holding device of claim 1, wherein a shape of the reflector holder is cylindrical, tapered cylindrical, or a combination of a cylindrical and tapered cylindrical.

12. The holding device of claim 1, wherein a diameter of a bottom surface of the reflector holder is substantially similar to a diameter of the first male extension.

13. The holding device of claim 12, further comprising a mechanism that joins a bottom surface of the reflector holder to a top surface of the first male extension to make a physical contact between the first end of the electromagnetic guiding device and a base of the extension.

14. The holding device of claim 13, wherein the mechanism joins a bottom surface of the reflector holder to a top surface of the first male extension to align a principal optical axis of the reflector with a principal optical axis of the electromagnetic guiding device.

15. The holding device of claim 13, wherein the mechanism comprises gold brazing.

16. The holding device of claim 1, wherein a top surface of the holder comprises a depression to place the reflector.

17. The holding device of claim 16, wherein the reflector is bonded to a top surface of the depression using a preform.

18. The holding device of claim 16, wherein the reform is a glass to metal sealing.

19. A holding device, comprising:
   a reflector comprising an extension extending out of a hypothetical base of the reflector;
   a reflector holder that receives the extension extending out of the hypothetical base of the reflector;
   a male connector comprising a first male extension and a second male extension that extend out of opposite surfaces of a male central disk;
   an electromagnetic guiding device continuously passing through a central hole that continuously passes through the first male extension, the male central disk and the second male extension; and
   a mechanism that joins a bottom surface of the reflector holder to a top surface of the first male extension to make a physical contact between a first end of the electromagnetic guiding device and a base of the extension.

20. The device of claim 19, wherein the mechanism substantially aligns a principal optical axis of the reflector to a principal optical axis of the electromagnetic guiding device.

\* \* \* \* \*